US00PP23143P2

(12) United States Plant Patent
Verschoor

(10) Patent No.: US PP23,143 P2
(45) Date of Patent: Oct. 23, 2012

(54) ***ASTILBE* PLANT NAMED 'VERSRED'**

(50) Latin Name: ***Astilbe arendsii*×*Astilbe japonica***
Varietal Denomination: Versred

(76) Inventor: Jan Verschoor, Haarlem (NL)

( * ) Notice: Subject to any disclaimer, the term of this patent is extended or adjusted under 35 U.S.C. 154(b) by 0 days.

(21) Appl. No.: 13/136,892

(22) Filed: Aug. 12, 2011

(51) Int. Cl.
*A01H 5/00* (2006.01)

(52) U.S. Cl. ..... Plt./407

(58) Field of Classification Search ..... Plt./407
See application file for complete search history.

*Primary Examiner* — Kent L Bell
(74) *Attorney, Agent, or Firm* — C. A. Whealy

(57) ABSTRACT

A new and distinct cultivar of *Astilbe* plant named 'Versred', characterized by its compact, broadly upright and mounding plant habit; strong and durable leaves; freely and uniformly flowering habit; red purple-colored flowers; and good container and garden performance.

2 Drawing Sheets

Botanical designation: *Astilbe arendsii*×*Astilbe japonica*.
Cultivar denomination: 'VERSRED'.

BACKGROUND OF THE INVENTION

The present invention relates to a new and distinct cultivar of *Astilbe*, botanically known as *Astilbe arendsii*×*Astilbe japonica* and hereinafter referred to by the name 'Versred'.

The new *Astilbe* plant is a product of a planned breeding program conducted by the Inventor in Haarlem, The Netherlands. The objective of the breeding program was to create new uniform and freely flowering *Astilbe* plants with attractive leaf and flower coloration.

The new *Astilbe* plant originated from a cross-pollination made by the Inventor in 2003 in Haarlem, The Netherlands, of an unnamed *Astilbe arendsii* seedling selection, not patented, as the female, or seed, parent with an unnamed *Astilbe japonica* seedling selection, not patented, as the male, or pollen, parent. The new *Astilbe* plant was discovered and selected by the Inventor as a single flowering plant from within the progeny of the stated cross-pollination in a controlled greenhouse environment in Haarlem, The Netherlands in 2005.

Asexual reproduction of the new *Astilbe* plant by in vitro propagation in a controlled environment in Honselersdijk, The Netherlands since the summer of 2005, has shown that the unique features of this new *Astilbe* plant are stable and reproduced true to type in successive generations.

SUMMARY OF THE INVENTION

Plants of the new *Astilbe* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Versred'. These characteristics in combination distinguish 'Versred' as a new and distinct *Astilbe* plant:

1. Compact, broadly upright and mounding plant habit.
2. Strong and durable leaves.
3. Freely and uniformly flowering habit.

4. Red purple-colored flowers.
5. Good container and garden performance.

Plants of the new *Astilbe* differ primarily from plants of the parent selections in plant height and flowering habit as plants of the new *Astilbe* are more compact and more freely flowering than plants of the parent selections.

Plants of the new *Astilbe* can be compared to plants of *Astilbe arendsii* 'Fanal', not patented. In side-by-side comparisons conducted in Haarlem, The Netherlands, plants of the new *Astilbe* and 'Fanal' differed in the following characteristics:

1. Plants of the new *Astilbe* were more compact than plants of 'Fanal'.
2. Plants of the new *Astilbe* had better container performance than plants of 'Fanal'.
3. Plants of the new *Astilbe* were more freely flowering than plants of 'Fanal'.
4. Flowers of plants of the new *Astilbe* and 'Fanal' differed slightly in color.

BRIEF DESCRIPTION OF THE PHOTOGRAPHS

The accompanying colored photographs illustrate the overall appearance of the new *Astilbe* plant showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet comprises a side perspective view of a typical flowering plant of 'Versred' grown in an outdoor nursery.

The photograph at the top of the second sheet is a close-up view of typical inflorescences of 'Versred'.

The photograph at the bottom of the second sheet is a close-up view of the upper surface of typical leaves of 'Versred'.

DETAILED BOTANICAL DESCRIPTION

The aforementioned photographs and following observations, measurements and values describe plants grown during the spring and early summer in an outdoor nursery in Hillegom, The Netherlands and under cultural practices typical of commercial *Astilbe* production. During the production of the plants, day temperatures ranged from 14° C. to 28° C. and night temperatures ranged from 4° C. to 18° C. Plants were three years old when the photographs and description were taken. In the following description, color references are made to The Royal Horticultural Society Colour Chart, 2007 Edition, except where general terms of ordinary dictionary significance are used.

Botanical classification: *Astilbe arendsii*×*Astilbe japonica* 'Versred'.

Parentage:

*Female, or seed, parent*.—Unnamed *Astilbe arendsii* seedling selection, not patented.

*Male, or pollen, parent*.—Unnamed *Astilbe japonica* seedling selection, not patented.

Propagation:

*Type*.—By divisions.

*Time to initiate roots*.—About three weeks at 20° C.

*Root description*.—Thick, fleshy; brown in color.

*Rooting habit*.—Freely branching; dense.

Plant description:

*Plant form and growth habit*.—Herbaceous perennial; compact, broadly upright and mounding plant form with inflorescences held above the foliar plane; flowering stems and leaves basal; freely flowering with about 29 basal branches developing per plant, dense and bushy; low vigor to moderately vigorous growth habit; and freely and uniformly flowering habit.

*Growth rate*.—Moderate; from divisions, about 20 weeks are required to produce fully-grown flowering plants in containers.

*Plant height* (*soil level to top of foliar plane*).—About 28 cm.

*Plant height* (*soil level to top of inflorescences*).—About 41.5 cm.

*Plant width* (*spread*).—About 43.2 cm.

*Stem description*.—Length: About 26.7 cm. Diameter: About 2 mm. Internode length: About 8.4 cm. Strength: Strong. Texture: Smooth, glabrous. Color: Close to 143C.

Foliage description:

*Arrangement*.—Alternate; biternately compound; about nine leaflets per leaf.

*Leaf length* (*excluding petiole*).—About 11.8 cm.

*Leaf width*.—About 10.7 cm.

*Lateral leaflet length*.—About 3.8 cm.

*Lateral leaflet width*.—About 2.3 cm.

*Terminal leaflet length*.—About 4.6 cm.

*Terminal leaflet width*.—About 2.9 cm.

*Lateral and terminal leaflet shape*.—Ovate to broadly ovate.

*Lateral and terminal leaflet apex*.—Acute.

*Lateral and terminal leaflet base*.—Cuneate to obtuse.

*Lateral and terminal leaflet margin*.—Biserrate.

*Lateral and terminal leaflet texture, upper and lower surfaces*.—Sparsely pubescent; moderately rugose.

*Lateral and terminal leaflet venation pattern*.—Pinnate.

*Lateral and terminal leaflet color*.—Developing leaflets, upper surface: Close to N137C. Developing leaflets, lower surface: Close to 137B to 137C. Fully expanded leaflets, upper surface: Close to N137A and N137B; venation, close to 144A to 144B. Fully expanded leaflets, lower surface: Close to 137C; venation, close to 147C.

*Leaf petiole length*.—About 9.5 cm.

*Leaf petiole diameter*.—About 1 mm.

*Leaflet petiole length*.—About 9 mm.

*Leaflet petiole width*.—About 0.75 mm.

*Leaf and leaflet petiole texture, upper and lower surfaces*.—Smooth, glabrous.

*Leaf and leaflet petiole color, upper and lower surfaces*.—Close to 144B to 144C.

Flower description:

*Flower type and flowering habit*.—Single rotate flowers arrange on terminal branched compound racemes; flowers face upright, outward or downward depending on position on the inflorescence; racemes roughly conical in shape; freely and uniformly flowering habit with about 600 flowers per inflorescence.

*Fragrance*.—Moderately faint; somewhat sweet.

*Natural flowering season*.—Plants begin flowering about ten months after planting; continuously flowering from early to late summer in The Netherlands.

*Postproduction longevity*.—Flowers last about ten days on the plant; flowers persistent.

*Flower buds*.—Height: About 2 mm. Diameter: About 1.5 mm. Shape: Broadly elliptic. Color: Close to 61C.

*Inflorescence height*.—About 9.1 cm.

*Inflorescence diameter*.—About 6.5 cm.

*Flower diameter*.—About 5 mm.

*Flower depth*.—About 2.5 mm.

*Petals*.—Quantity per flower: Typically five in a single whorl. Length: About 2.5 mm. Lobe width: About 0.5 mm. Shape: Oblanceolate. Apex: Broadly acute. Margin: Entire. Texture, upper and lower surfaces: Smooth, glabrous. Color: Developing petals, upper and lower surfaces: Close to 64B. Fully expanded petals, upper and lower surfaces: Close to 64B; color becoming lighter than 71D with development.

*Sepals*.—Quantity per flower: Typically five in a single whorl, fused towards the base; campanulate-shaped calyx. Length: About 1.5 mm. Width: About 0.7 mm. Shape: Ovate. Apex: Acute. Base: Cuneate. Margin: Entire. Texture, upper and lower surfaces: Smooth, glabrous. Color: Developing sepals, upper and lower surfaces: Close to 146A tinged with close to 60B to 60C. Fully expanded sepals, upper and lower surfaces: Close to 75D; towards the apex and margins, close to 61B.

*Peduncles*.—Length: About 8.8 cm. Diameter: About 1 mm. Angle: Erect. Strength: Strong. Texture: Smooth, glabrous. Color: Close to 146C; towards the apex, strongly tinged with close to 185D.

*Pedicels*.—Length: About 0.5 mm. Diameter: About 0.4 mm. Angle: About 45° from vertical. Strength: Moderately strong. Texture: Smooth, glabrous. Color: Close to 61B.

*Reproductive organs*.—Stamens: Quantity per flower: Typically ten; anthers basifixed. Filament length: About 1 mm. Filament color: Close to 64B. Anther shape: Ovate. Anther length: About 0.3 mm. Anther color: Close to 62B. Pollen amount: Scarce. Pollen color: Close to 155D. Pistils: Quantity per flower: Two. Pistil length: About 0.2 mm. Stigma shape: Club-shaped. Stigma color: Close to 61A. Style length: About 0.1 mm. Style color: Close to 61B. Ovary color: Close to 61B.

*Seeds and fruits*.—Seed and fruit development have not been observed on plants of the new *Astilbe*.

Disease & pest resistance: Plants of the new *Astilbe* have not been noted to be resistant to pathogens and pests common to *Astilbe* plants.

Garden performance: Plants of the new *Astilbe* have been observed to have good garden performance and tolerate rain, wind and high temperatures of about 35° C. Plants of the new *Astilbe* have been observed to be hardy to USDA Hardiness Zone 5.

It is claimed:

1. A new and distinct *Astilbe* plant named 'Versred' as illustrated and described.

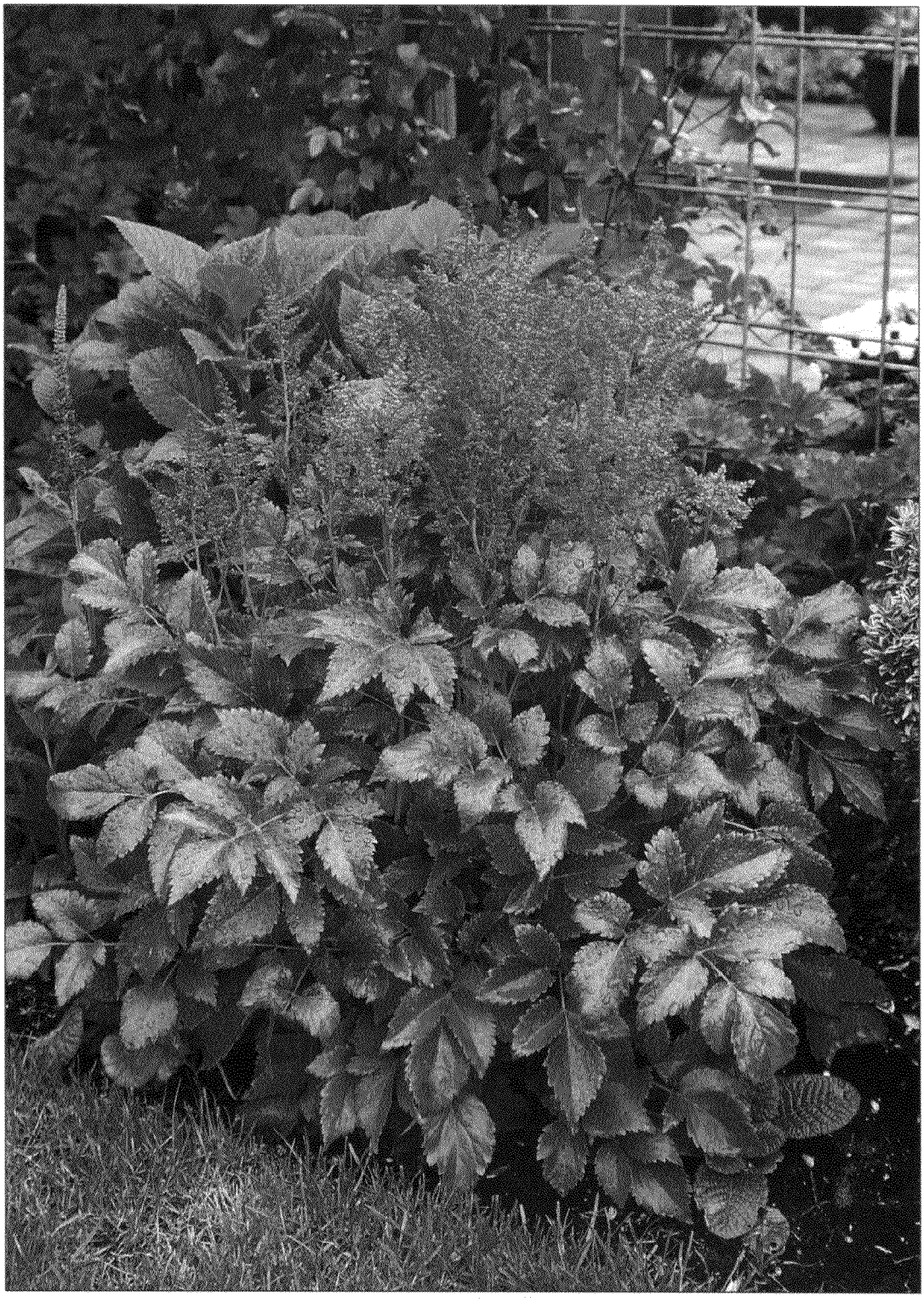

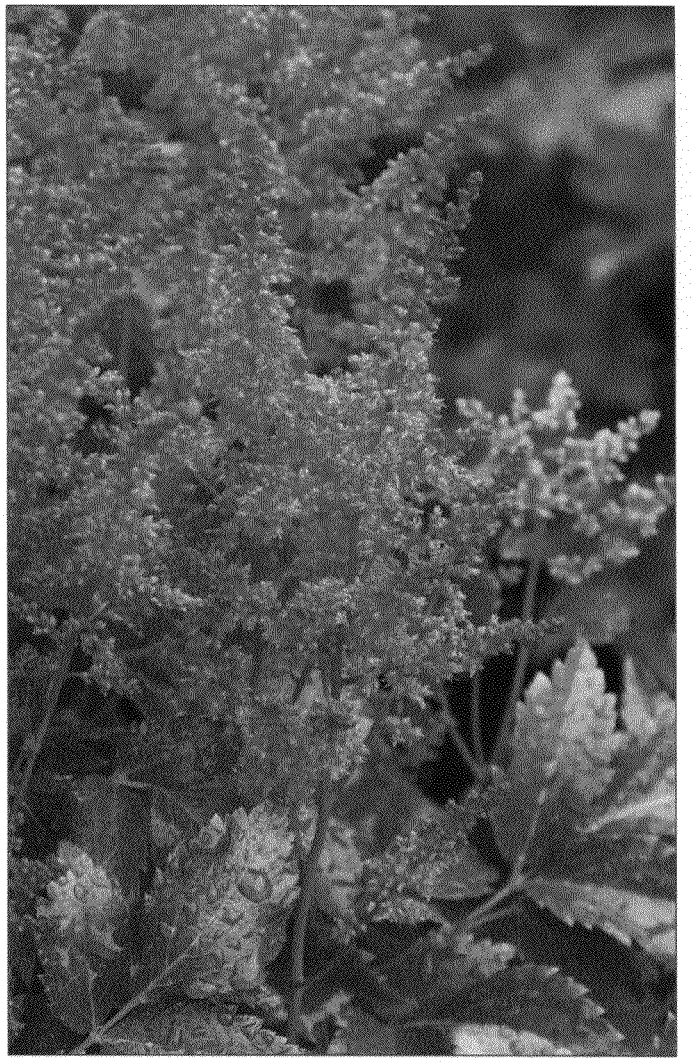
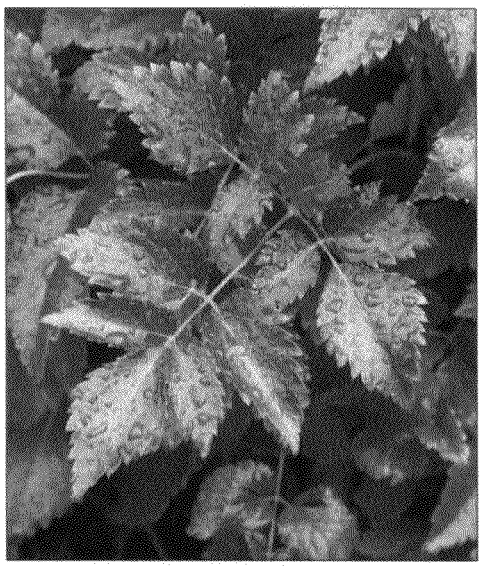

* * * * *